United States Patent [19]
Blumbergs et al.

[11] Patent Number: 5,110,919
[45] Date of Patent: May 5, 1992

[54] PROCESS FOR THE PREPARATION OF 2-AMINO-9-(2,3,5-TRI-O-BENZYL-BETA-D-ARABINOFURANOSYL) ADENINE AND NOVEL INTERMEDIATES

[75] Inventors: Peter Blumbergs, Royal Oak; Mohammed S. Khan, Detroit; Richard L. Kalamas, Wyandotte, all of Mich.

[73] Assignee: Ash Stevens, Inc., Detroit, Mich.

[21] Appl. No.: 445,446

[22] Filed: Dec. 4, 1989

[51] Int. Cl.$^5$ .................. C07H 19/16; C07H 19/19; C07D 473/00; C07D 473/02

[52] U.S. Cl. ........................................ 536/24; 536/26; 544/264; 544/265

[58] Field of Search ................ 536/24, 26; 544/263-268

[56] References Cited

U.S. PATENT DOCUMENTS 3,008,969 11/1961 Pretka ........................... 549/288
4,188,378 2/1980 Montgomery ..................... 514/46

OTHER PUBLICATIONS

Chemical Abstracts, vol. 104, No. 19, No. 168743j.
Groziak et al. J. Org. Chem. vol. 51, No. 8, pp. 1277-1282.
Montgomery et al., in J. Hetero. Chem. 16, 157 (1979).

*Primary Examiner*—Johnnie R. Brown
*Assistant Examiner*—Gary L. Kunz
*Attorney, Agent, or Firm*—Ian C. McLeod

[57] ABSTRACT

A process for the preparation of 2,6-diamino-9-(2,3,5-tri-O-benzyl-beta-D-arabinofuranosyl)purine (V) by reacting 2,6-di(alkoxyacetamido)purine (II) with 2,3,5-tri-O-benzyl-1-chloro-alpha-D-arabinofuranose (III) to produce 2,6-di(alkoxyacetamido)-9-(2,3,5-tri-O-benzyl-beta-D-arabinofuranosyl)purine (IV) and then deprotecting the 2,6-positions to produce the 2,6-diamine (V) is described. The process provides purine (V) in high yield. Purine (V) is an intermediate in the preparation of 9-beta-D-arabinofuranosyl-2-fluoroadenine which is a cytotoxic agent.

18 Claims, No Drawings

PROCESS FOR THE PREPARATION OF 2-AMINO-9-(2,3,5-TRI-O-BENZYL-BETA-D-ARABINOFURANOSYL) ADENINE AND NOVEL INTERMEDIATES

BACKGROUND OF THE INVENTION (1) Field of the Invention

The present invention relates to a process for the preparation of 2-amino-9-(2,3,5-tri-O-benzyl-beta-D-arabinofuranosyl)adenine (V) and certain novel intermediate compounds which are useful in the preparation of 2-fluoro-ara-AMP, a cytotoxic agent. In particular the present invention relates to a process wherein a protected compound 2,6-di(alkoxyacetamido)purine (II) is reacted with 2,3,5-tri-O-benzyl-alpha-D-arabinofuranosyl chloride (III) to produce 2,6-di(alkoxyacetamido)-9-(2,3,5-tri-O-benzyl-beta-D-arabinofuranosyl)purine (IV) and then the alkoxyacetyl groups are removed to produce the title sugar-protected compound V in high yield.

(2) Prior Art

Example 2B of U.S. Pat. No. 4,188,378 (Feb. 12, 1980) to John A. Montgomery shows the preparation of 2-amino-9-(2,3,5-tri-O-benzyl-beta-D-arabinofuranosyl) adenine (V). To accomplish this 2,3,5-tri-O-benzyl-1-O-p-nitrobenzoyl-beta-D-arabinofuranose was converted to the furanosyl chloride (III) in ethylene chloride and reacted with 2,6-diacetamidopurine (II). The resulting intermediate (IV) was then treated with sodium methoxide in methanol to remove the two acetyl groups and produce the target 2-aminoadenine (V) in 34% yield overall. This is the same route reported earlier by Montgomery et al. in J. Hetero. Chem. 16, 157 (1979), in which the reported overall yield was 40%. This method is clearly a low yield process. In example 2A of the cited patent, Montgomery prepared Compound (V) by an alternative sequence of reactions. These involved the prior preparation (not shown) of 2,6-dichloropurine which was then treated with sodium azide in ethanol to yield the 2,6-diazidopurine as described in Example 1. This was followed by catalytic hydrogenation to obtain Compound (V). This is clearly a longer, less desirable route.

OBJECTS

It is therefore an object of the present invention to provide a process for the preparation of 2,6-diamino-9-(2,3,5-tri-O-benzyl-beta-D arabinofuranosyl) purine (V) in high yield. Further, it is an object of the present invention to provide novel intermediates. Further still, it is an object of the present invention to provide a process which is economical. These and other objects will become increasingly apparent by reference to the following description.

GENERAL DESCRIPTION

The present invention relates to a process for the preparation of the compound 2,6-diamino-9-(2,3,5-tri-O-benzyl-beta-D-arabinofuranosyl) purine (V) which comprises:

(a) reacting a 2,6-di(alkoxyacetamido) purine (II) with 2,3,5-tri-O-benzyl-alpha-D-arabinofuranosyl chloride (III), wherein alk is a lower alkyl group containing 1 to 6 carbon atoms which can be straight chain or branched, in a non-polar water-insoluble organic solvent in the presence of a hydrochloric acid acceptor to produce 2,6-di(alkoxyacetamido)-9-(2,3,5-tri-O-benzyl-beta-D-arabino furanosyl)purine (IV) in a first reaction mixture;

(b) separating intermediate (IV) from the first reaction mixture by removing the non-polar organic solvent; and (c) removing 2,6-dialkoxyacetyl groups from intermediate (IV) to produce the Compound (V). The compound 2,6-di(methoxyacetamido)purine is preferred as compound (II).

The present invention relates to the novel intermediate compound 2,6-di(alkoxyacetamido)-9-(2,3,5-tri-O-benzyl-beta-D-arabinofuranosyl)purine (IV), where alk is preferably a methyl group. Intermediate (IV), a syrup was obtained in quantitative yield and is readily converted with sodium methoxide to form target compound (V) in high yield by the process of the present invention.

The alk groups in intermediates (II) and (IV) are selected from methyl, ethyl, propyl, butyl, pentyl or hexyl groups which can be straight chain or branched. Methyl is preferred.

The non-polar solvent in step (a) can be dichloroethane or acetonitrile.

The reaction in step (a) is preferably conducted at a temperature between about 80° to 85° C. Elevated temperatures between about 75° and 100° C. can be used. The reaction mixture is usually refluxed for at least about 18 hours in the solvent.

The acid acceptor can be any compatible amine or other Lewis base. Diisopropylethylamine is preferred. Molecular sieves can also be used.

The water is removed from the reaction mixture in step (b). Various dehydrating agents such as n-propanol can be used.

In step (c) the reaction mixture is held at a temperature between about 45° C. and 55° C. in the lower alkanol for the reaction to remove the 2,6-dialkoxylacetyl groups and to provide the 2,3,5-tri-O-benzyl-2,6-diaminopurine (IV). The lower alkanol can be methyl or ethyl alcohol. Other methods for the removal of these groups are methylamine in methanol or ammonia, methanol or ethanol, both in closed systems.

SPECIFIC DESCRIPTION

The eight-step sequence for the preparation of 2-fluoro-ara-AMP via the improved process is as follows:

Reaction Sequence
2-Fluoro-ara-AMP (Fludarabine Phosphate)

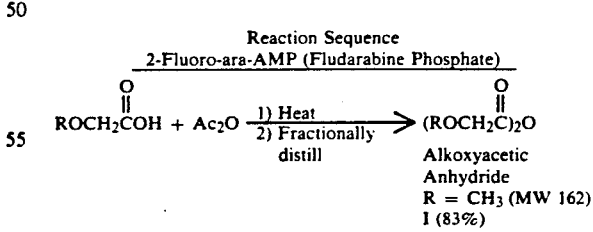

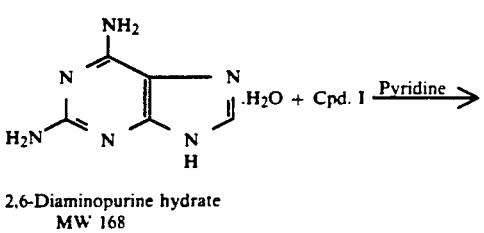

2,6-Diaminopurine hydrate
MW 168

-continued
Reaction Sequence
2-Fluoro-ara-AMP (Fludarabine Phosphate)

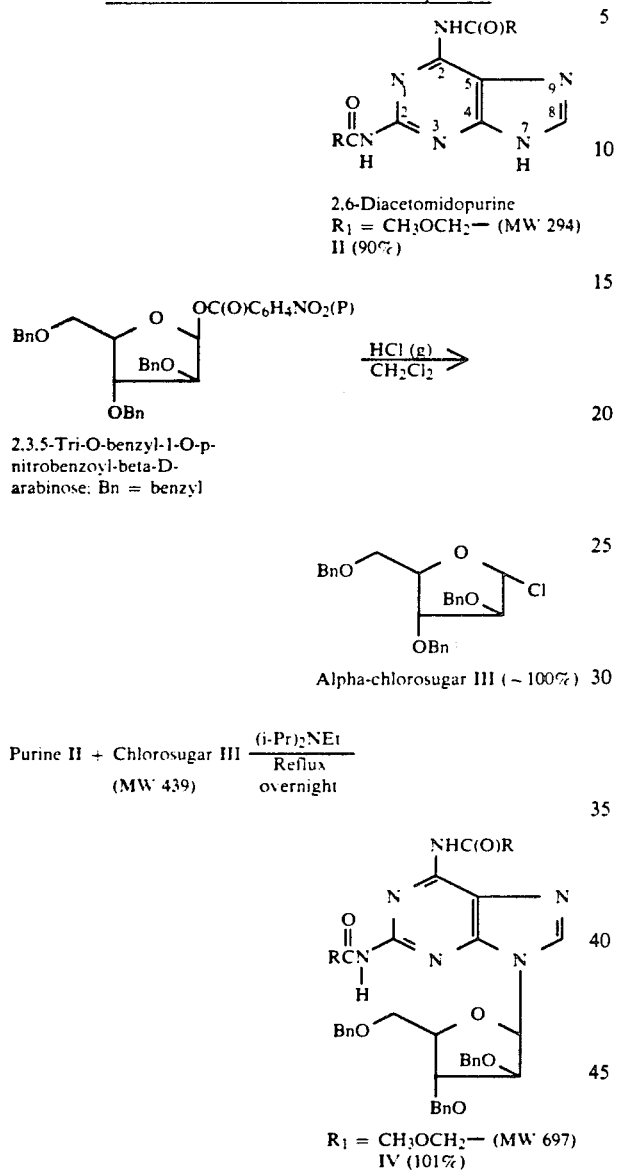

2,6-Diacetomidopurine
$R_1 = CH_3OCH_2—$ (MW 294)
II (90%)

2,3,5-Tri-O-benzyl-1-O-p-nitrobenzoyl-beta-D-arabinose; Bn = benzyl

Alpha-chlorosugar III (~100%)

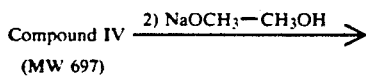

$R_1 = CH_3OCH_2—$ (MW 697)
IV (101%)

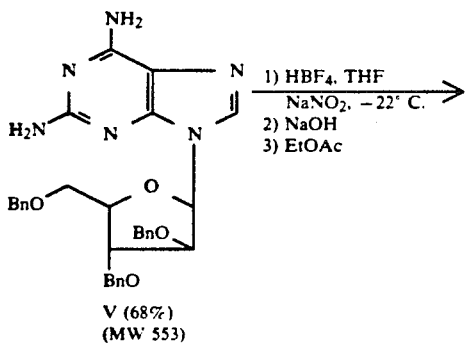

V (68%)
(MW 553)

-continued
Reaction Sequence
2-Fluoro-ara-AMP (Fludarabine Phosphate)

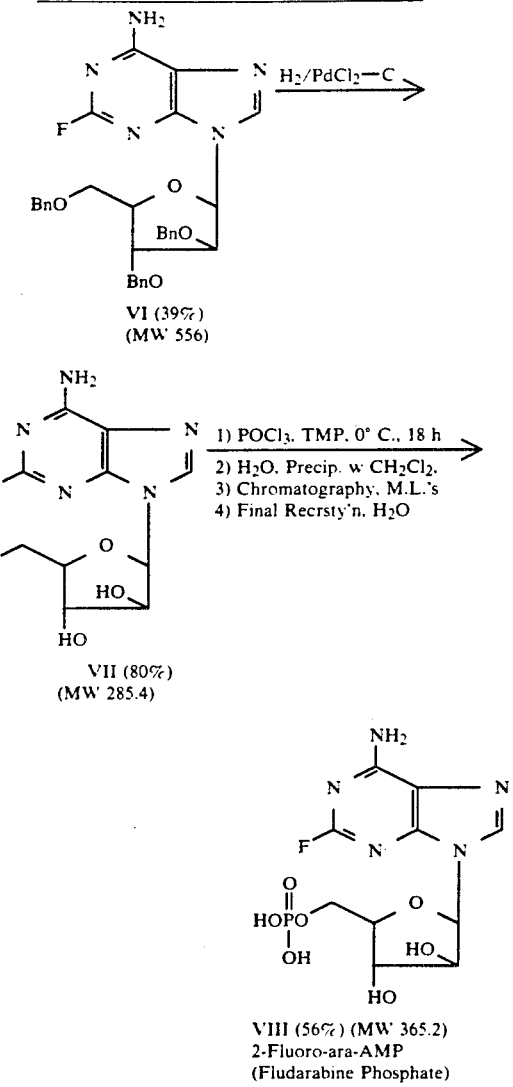

VI (39%)
(MW 556)

VII (80%)
(MW 285.4)

VIII (56%) (MW 365.2)
2-Fluoro-ara-AMP
(Fludarabine Phosphate)

The most significant improvement in the process is the replacement of the two protecting acetyl groups with methoxyacetyl groups for 2,6-diaminopurine. 2,6-Di(methoxyacetamido)purine (II), prepared in 90% yield from 2,6-diaminopurine and methoxyacetic anhydride (I), coupled extremely well with the protected 1-chloro-alpha-D-arabinose to give an essentially 100% yield of the coupled product (IV). This is in sharp contrast with 2,6-diacetamidopurine which coupled with the chloro sugar in but 34 to 40% yield as described above in the Prior Art. Furthermore, the reaction time was reduced to 16–18 hours (overnight) as opposed to five days, and the molecular sieves (which disintegrate during the reaction) could be replaced with diisopropylethylamine as the acid acceptor.

In addition, the high solubility of intermediate (II) allowed a ten-fold reduction in the volume of solvent (ethylene dichloride) used in the coupling step, thus greatly facilitating the large scale preparation of intermediate (IV).

The low temperature diazotization-fluorination of the protected diamine (V) to the 2-fluoro derivative (VI) was studied sufficiently to permit the reaction to be scaled to the 300 g level and, less advantageously, to the 500 g level. The hydrogenation-debenzylation conversion of the protected nucleoside (VI) to nucleoside (VII) again went well in 80% average yield; the less expensive palladium chloride was used in presence of activated carbon to essentially simulate palladium on carbon catalyst.

Furthermore, previous reports (Montgomery, U.S. Patent and J. Het. Chem previously cited) state that catalytic hydrogenation results in partial defluorination. The procedure described herein where the hydrogenation is conducted in the presence of hydrochloric acid avoids defluorination and simplifies the purification procedure.

Finally, the problem of erratic yields occurring in the phosphorylation of the nucleoside (VII) to the target 5'-phosphate (VIII) was solved by utilizing essentially anhydrous nucleoside. While the time to achieve reaction homogeneity was extended from 20 minutes to nearly three hours, reproducible yields of 75–79% (average 76%) of good quality product were achieved. It was found that care must be taken to provide a trace of moisture in the reaction mixture to maintain good yields.

EXPERIMENTAL

Methoxyacetic anhydride (I)

A mixture of methoxyacetic acid (360 g, 4 mol) and acetic anhydride (409 g, 4 mol) was heated with stirring in a 2 L 3-neck flask equipped with a bubble-plate distillation column and a fraction cutter. A mixture of acetic acid and acetic acid anhydride was distilled at atmospheric pressure until the internal temperature reached 164° C. The pressure was reduced and the product was collected at 65°–71° C. at 0.2 mmHg to give 229 g (71%) of pure title compound. A total of 34.8 kg of methoxyacetic acid was processed to give 26.1 kg (83%) of the anhydride (I).

| Materials |
| --- |
| Methoxyacetic acid |
| Acetic anhydride |

2,6-Di(methoxyacetamido)purine (II)

A mixture 2,6-diaminopurine monohydrate (504 g, 3.0 mol) and methoxyacetic anhydride (1.53 kg, 9.46 mol) in pyridine (3.5 L) was heated (steam bath) with stirring. The temperature rose to 88° C. in about 10 minutes and the mixture became homogeneous; then the temperature rose spontaneously to 103° C. (exotherm). The reaction mixture was stirred for one hour during which time the temperature dropped to 97° C. and solid started to precipitate. Heating was discontinued and the reaction temperature fell to 58° C. The mixture was gradually diluted with methyl ethyl ketone (3.5 L) and then stirred slowly overnight. The solid was collected and the filter cake was washed with methyl ethyl ketone (800 mL). The cake was transferred to a beaker and stirred with methyl ethyl ketone (6 L). The solid product was collected by filtration, washed with methyl ethyl ketone (2 L) and air-dried overnight. The air-dried material was then dried to constant weight at 80°–85° C./0.3 mmHg for 18 hours to give 790 g (90%) of the title diamide (II), mp 219°–220° C.

In this manner a total of 7.35 kg of 2,6-diaminopurine and 22.33 kg of methoxyacetic anhydride (I) were processed to yield 11.70 kg (91%) of the title diamide II.

Anal. Calcd. for $C_{11}H_{14}N_6O_4$(294.27): C, 44.89; H, 4.79; N, 28.56. Found: C, 44.91; H, 4.71; N, 28.36.

| Materials |
| --- |
| 2,6-Diaminopurine |
| Methyl ethyl ketone |
| Methoxyacetic anhydride |
| Pyridine |

2,3-5-Tri-O-benzyl-alpha-D-arabinosyl chloride (III)

Hydrogen chloride gas was bubbled into a mechanically-stirred solution of 2,3,5-tri-O-benzyl-1-O-p-nitrobenzoyl-beta-D-arabinofuranose (1.25 kg, 2.2 mol) in methylene chloride (6.25 L) at 4°–6° C. for two hours. The reaction mixture was warmed to 16° C., and the mixture purged with $N_2$ for 10 minutes and filtered through a sintered glass dispersion tube. The residual solid p-nitrobenzoic acid was washed with methylene chloride (2 × 1.25L). The solvent was removed (aspirator) with stirring at 23°–27° C. (internal) until most of the methylene chloride was removed. Ethylene dichloride (EDC, 1.25 L) was added and then removed (aspirator) to an internal temperature of 37° C.

Titration of the liberated p-nitrobenzoic acid indicated the the yield of the chloro sugar III was essentially quantitative in agreement with the weight of the syrup, 975 g 101%.

| Materials |
| --- |
| 2,3,5-Tri-O-benzyl-1-O-p-nitrobenzoyl beta-D-arabinose |
| Methylene chloride |
| Hydrogen chloride, gas |
| Ethylene dichloride |

2,6-Di(methoxyacetamido)-9-(2,3,5-tri-O-benzyl-beta-D-arabinofuranoxyl)purine (IV)

2,6-Di(methoxyacetamido)purine (II) (646 g, 2.20 mol) was suspended in ethylene dichloride (EDC) (4.8 L). The mixture was dried by removing 600 mL of the EDC by distillation. The concentrated solution of the above-prepared alpha-chloro sugar III (2.20 mol) was added to the suspension, followed by freshly-distilled diisopropylethylamine (354 g, 2.75 mol). The mixture was refluxed overnight (steam bath) with stirring and the hot solution was poured into deionized water (4 L) with stirring. The organic phase was separated and the aqueous phase was washed with EDC (1.5 L). The combined organic phase was washed with deionized water (2 × 2 L). EDC was removed (aspirator, steam bath) with stirring. The residue was azeotroped with n-propanol (2 L) which was removed by distillation to give compound IV as a syrup. The yield was 1.55 kg, 101%, essentially quantitative.

| Materials |
| --- |
| 2,6-Di(methoxyacetamido)purine (II) |
| Alpha-chlorosugar (III) |
| Ethylene dichloride |
| Diisopropylethylamine |

2-Amino-9-(2,3,5-tri-O-benzyl-beta-D-arabinofuranosyl)adenine (V)

The protected 2,6-di(methoxyacetamido)purine (IV) (1.55 kg, 2.20 mol) was dissolved in methanol (3.6 L) with stirring and warmed to 46°–48° C. A solution of sodium methoxide (30 g, 95%, 0.55 mol, in 250 mL methanol) was added and the solution was warmed to 61° C. The reaction was completed in about 1 hour (tlc) at which time the product started to precipitate. The mixture was allowed to cool to 30° C. and then refrigerated overnight. The product was collected, washed with ice-cold methanol (800 mL) and air-dried to give the title compound (V) 823 g (68%), mp 160°–162° C.

| Materials |
| --- |
| Intermediate (IV) |
| Sodium methoxide (95%) |
| Methanol, abs. (R) |
| Ether, anhydrous (R) |

9-(2,3,5-Tri-O-benzyl-beta-D-arabinofuranosyl)-2-fluoroadenine (VI)

A mechanically-stirred suspension of the protected nucleoside V (300 g, 0.543 mol) in tetrahydrofuran (1.125 L) was cooled to −32° C. (dry ice-acetone). Fluoroboric acid (48%, 150 mL) was added over a period of 35–40 minutes. The temperature rose during the addition to −23° C. to −21° C. where it was maintained by cooling. A solution of sodium nitrite (62 g, 0.899 mol) in water (75 mL) was added over a period of 10 minutes, followed by the remaining fluoroboric acid (1 L) over a period of 55 minutes while maintaining the temperature between −23° C. to −21° C. throughout. The mixture was stirred for 2.5 hours at −23° C. to −21° C., then poured with stirring into a mixture of ethyl acetate (1.5 L) and ice (1.5 kg). A 50% solution of sodium hydroxide (510 mL) in water was added to adjust the pH to 8. The ethyl acetate phase was separated and the aqueous phase was extracted with ethyl acetate (1 L, 600 mL). The ethyl acetate phase and extract were combined, washed with deionized water (2 × 500 mL) and concentrated (aspirator, steam bath). The residue was azeotroped with benzene (2 × 750 mL) and the semisolid mass was dissolved in ethanol (360 mL). Benzene (70 mL) was added to the solution which was stirred and allowed to cool to 43° C. when solid material began to precipitate. At this point cold ethanol saturated with ammonia (360 mL) was added and the mixture was cooled rapidly to 24° C. (ice-bath). The mixture was then stored in the refrigerator overnight. The precipitate was collected, washed with ethanol (250 mL) and with petroleum ether (400 mL) and air-dried to give 129 g of crude product, mp 155°–7° C., containing organic by-products and residual salts.

In this manner, 3.10 kg of starting material (V) was processed to give 1.25 kg (40.1%) of crude product (VI). This was recrystallized as described below (Method A) to yield 1.00 kg (32.1%) of purifed product, mp 156.5°–158° C. and a second crop, 80 g (2.6%). Also, in the same manner, 2.40 kg of precursor V was processed to give 1.02 kg (42.3 %) of crude VI. A second crop, 100 g, was isolated from the mother liquors. The 1.02 kg of crude (VI) was combined with the above 80 g second crop and recrystallized (Method B) to give 910 g of purified product and 97 g of a second crop. Thus a total of 5.50 kg of precursor (V) was processed to give 1.91 kg (34.5%) of pure material used in the next step plus 207 g (3.7%) of second crop material.

Purification Procedures for Compound (VI)

Method A

The crude product (1.25 kg) was dissolved in 90% ethanol-benzene (10 mL/g; preheated to reflux) in two batches, 900 g and 350 g. Norit A (87.5 g) was added to the hot solution which was filtered through a celite pad using a steam-jacketed funnel. The filter cake was washed with 90% ethanol-benzene (1 L). The combined filtrate was allowed to cool to room temperature overnight. The solids were collected, washed with ethanol (1 L) and with petroleum ether (1.5 L) and dried at 60° C. at 0.3 mmHg for 2 hours to give 1.00 kg of purified product, mp 156°–58° C. The mother liquor was concentrated to 1.8 L (aspirator, steam bath). The precipitated solids were dissolved by heating the mixture to reflux. The solution was allowed to cool to room temperature. The resulting mixture was filtered to give 80 g of second crop material.

Method B

The procedure was the same as above except that the recrystallization solvent was 92% ethanol-toluene (10 mL/g) instead of 90% ethanol-benzene (10 mL/g).

| Materials |
| --- |
| 2-Amino-9-(2,3,5-tri-O-benzyl-beta-D-arabinofuranosyl)adenine (V) |
| THF |
| Fluoroboric acid (48%) |
| Sodium nitrite |
| Ethyl acetate |
| Sodium hydroxide, 50% aq. |
| Ethanol, 3A, specially denatured |
| Ammonia, gas |
| Benzene |
| Toluene |
| Petroleum ether (35–60° C.) |
| Norit A, acid-washed |
| Celite, analytical grade |

9-beta-D-Arabinofuranosyl-2-fluoroadenine (VII)

Concentrated hydrochloric acid (0.5 mL/g of nucleoside, 50 mL, 0.608 mol) was added to a suspension of intermediate VI (100 g, 0.180 mol) in methoxyethanol (500 mL) to give a homogeneous yellow solution to which palladium chloride (3.0 g) and Norit A (10 g) were added. The mixture was flushed with hydrogen (2 × 20 psig) and the hydrogen pressure was raised to 50 psig. After 10 minutes the pressure which had fallen to 2 psig was adjusted back to 50 psig. The process was repeated twice more until there was no further hydrogen uptake (total time, 50 minutes). No starting material was present by tlc. The catalyst was removed through a celite bed and the filter cake was washed with methoxyethanol (2 × 50 mL). The filtrate was cooled (ice-bath) and concentrated ammonium hydroxide (~55 mL) was added to pH ~8 (light-pink color). The precipitate (NH$_4$Cl) was removed by filtration and the filtrate was concentrated to near dryness. The resulting solid was slurried with water (150 mL), filtered and washed with ethanol (50 mL) to give 55 g of crude product (air-dried). The crude product was recrystallized from hot ethanol-water (1.6 L, 1:1 v/v) to afford, after air-drying, 44 g (81% as a monohydrate) of the title nucleoside VII, mp 264°-266° C. (dec).

In this manner a total of 3.15 kg of protected nucleoside was processed to give 1.53 kg of crude air-dried product. The crude product was recrystallized from hot ethanol-water (30 mL/g, 46 L, 1:1 v/v) and dried at 90° C., 0.3 mmHg for 24 hours to give pure anhydrous title compound (VII), 1.295 kg (80%, average yield), mp 264°-266° C. (dec); lambda max ($H_2O$) 261 nm ($\epsilon$ = 15,100).

Anal. Calcd for $C_{10}H_{12}FN_5O_4$ (285.24): C, 42.11; H, 4.24; F, 6.66; N, 24.55. Found: C, 42.00; H, 4.40; F, 6.60; N, 24.61.

| Materials |
| --- |
| 2-Methoxyethanol |
| Palladium chloride |
| Concd. hydrochloric acid (37.3%) |
| Norit A |
| Concd. ammonium hydroxide |
| Ethanol, 3A, specially denatured |
| Cellulose powder, CF-11 |

9-beta-D-Arabinofuranosyl-2-fluoroadenine 5'-phosphate (VIII) NSC 312887

A typical 100 g run used to process the final 785 g of intermediate (VII) is described. Phosphorous oxychloride (80.0 g, 49 mL, 523 mmol) was added to cold (0° C., ice-bath) trimethylphosphate (1 L) and the solution was kept at 0° C. for 1 hour. 9-beta-D-Arabinofuranosyl-2-fluoroadenine (VII) (100.0 g, 350.6 mmol) was added with stirring in one portion. The reaction mixture became homogeneous (light-yellow solution) after two hours and 50 minutes. The reaction mixture was then placed in a refrigerator (~1° C.) for 15 hours. No starting material was present by tlc. Water (70 mL) was added and the solution was stirred for 3 hours at 0° C. The mixture was then poured into cold (−0° C., ice-bath) methylene chloride (8 L) with stirring and held in the ice-bath with stirring until a clear methylene chloride phase was obtained (1 h) The methylene chloride was removed by decantation and the residual yellowish, gummy mass was dissolved in warm (~50° C.) water (700 mL). The solution was seeded and allowed to stand at room temperature overnight. The resulting crystalline product was collected by filtration and washed with water (50 mL) and with ethanol (2 × 50 mL). The product was dried at room temperature at 0.3 mmHg for 4 hours to give 78.5 g (tlc, trace impurities) of first crop material, mp 200°-205° C. (dec), with prior browning at ~185° C.

The methylene chloride supernatant liquid, which remained after the isolation of the crude gummy product, was extracted with water (3 × 500 mL) The water extracts were combined and percolated into a column containing Dowex-50 (acid form) resin (560 × 80 mm). The column was eluted with water and the fractions containing prduct (by UV monitor and tlc) were combined. The aqueous solution was then concentrated (aspirator) to a smaller volume (ca. 250 mL) and allowed to cool to ambient temperature overnight. The resulting crystalline solid was removed by filtration, washed with a small portion of water followed by ethanol, and dried as above to give 11.0 g of product with the same purity (by tlc) as that of first crop. In a similar manner the mother liquor from the first crop was treated as described above to give 10.5 g of product of the same purity (tlc) as the other crops. The combined yield was 100 g (70% calculated as the monohydrate).

In this manner, 785 g of well-dried (24 h, 90° C., 0.3 mmHg), essentially anhydrous starting nucleoside (VII) was processed to give 799 g (76%, calculated as a monohydrate) of good quality target compound (VIII). However, in the initial series of runs, 510 g of nucleoside as the monohydrate was processed to give but 351 g (54%). This corresponds to an overall yield of 1150 g (68%) from 1295 g of precursor (VII) (See Note 1).

Final Recrystallization (See Note 2)

The above material, 1134 g, in five batches was dissolved in preheated deionized water (82° C., 15 mL/g). The compound dissolved in 3-5 minutes at 73°-75° C. The solutions from the five batches was filtered through paper and the filtrate was transferred to a 22 L flask. The solution was stirred and cooled rapidly to 45°-50° C. to minimize product decomposition. At this point, the product started to crystallize and the mixture was allowed to cool slowly over about one hour until the precipitation was essentially complete (see Note 3). The solution was then cooled (water-bath) over 2 hours to 22° C. and then cooled (ice-bath) for one hour. The resulting precipitate (a milky slurry) was collected by filtration through filter-cloth in four batches which requires 6 hours to complete. The filter cake was washed successively with cold deionized water (1.25 L) and ethanol (1.8 L).

The product was dried at room temperature at 0.3 mmHg for 24 hours and weighed 916 g as an 0.8 hydrate at this point. The product was dried further at 55°-60° C. at 0.3 mmHg for 72 hours to give 881 g (82% recovery) of anhydrous material. The average yield was 56% from the precursor nucleoside VII. The mother liquor can be reworked and additional product isolated.

Note 1

In exploratory work the nucleoside (VII), after air-drying was dried under vacuum at room temperature for several days to yield a monohydrate. The monohydrate dissolved readily (~20 min) in the reaction medium as the reaction proceeded, the excess phosphorus oxychloride appeared adequate to destroy the water of hydration and the yields were 65-68%. In the current work the 10 g probe run and two of the next three 100 g runs gave acceptable yields. However, in the last two 100 g runs (ran simultaneously) the yields averaged 41% and trial runs were reinstituted to correct the problem.

First the nucleoside was dried 24 hours at 0.33 mmHg and 90° C. to give essentially anhydrous material. The trimethylphosphate reaction solvent was distilled and the forerun and tail fractions were discarded. With these changes the time to obtain a homogeneous reaction system was extended to 2 hours and 50 minutes, but the yields were both reproducible and markedly improved (75-79%, average 76%) based on product (VIII) as a monohydrate after drying at room temperature for 4 hours at 0.3 mmHg.

Note 2

In view of the extensive handling in the last step, a final recrystallization was necessary to remove any inadvertently-introduced water-insoluble impurities. The acidic product is, however, unstable in hot water. Some decomposition occurs during the recrystallization and no real improvement in purity results. With careful handling in the last step, it is possible that the final recrystallization can be avoided.

Note 3

If the temperature is allowed to fall to 32°-33° C. before precipitation is complete, the product will precipitate as a gel.

| Materials |
| --- |
| trimethylphosphate |
| Phosphorous oxychloride (d = 1.645) |
| Methylene chloride |
| Molecular sieves, 4A |
| Dowex 50W-X2, 50-100 mesh |
| Alcohol, 3A, specially denatured |

PHYSICAL AND ANALYTICAL DATA

2-Fluoro-ara-adenosine 5'-phosphate, NSC 312887

Lot No. 3

Melting Point: 202°-203° C. (dec), browns at 190° C.
Analysis: Calcd for $C_{10}H_{13}FN_5O_7P$ (365.21)

|   | Calcd | Found |
| --- | --- | --- |
| C | 32.89 | 32.77 |
| H | 3.59 | 3.74 |
| N | 19.17 | 19.04 |
| F | 5.20 | 4.96 |
| P | 8.48 | 8.40 |

| Ultraviolet Spectral Data: |   |
| --- | --- |
| (pH 7 Buffer) | lambda max ($H_2O$) 262 nm $\epsilon$ 14,900 |
| (0.1 N HCl) | lambda max ($H_2O$) 262 nm $\epsilon$ 13,100 |
| (0.1 N NaOH) | lambda max ($H_2O$) 261 nm $\epsilon$ 15,600 |
| Thin Layer Chromatograph: (EM Silica gel 60F-254, 240) | |
| iso-PrOH—$H_2O$—$NH_4OH$ (7:2:1), $R_f$ = 0.30, trace impurity | |
| n-PrOH—MeOH—$H_2O$—$NH_4OH$ (4:3:2:1), $R_f$ = 0.41, trace impurity | |
| MeOH—$H_2O$—$NH_4OH$ (75:25:1), $R_f$ = 0.70, trace impurity | |
| Solubility Data: 25° C., without heating (Ref 1). | |
| Free Acid: | |
| Water: | 9 mg/mL (8.7 and 9.3 mg/mL), 2 det'ns, pH ~2 |
| Ethanol: | Insoluble |
| Sodium Salt: | |
| Water: | >100 mg/mL (upper limit not determined) |

It is intended that the foregoing description be only illustrative of the present invention and that the present invention be limited only by the hereinafter appended claims.

I claim:

1. A process for the preparation of the compound 2,6-diamino-9-(2,3,5-tri-O-benzyl-beta-D-arabinofuranosyl) purine (V) which comprises:
   (a) reacting 2,6-di(alkoxyacetamido)purine (II) with 2,3,5-tri-O-benzyl-1-chloro-alpha-D-arabinofuranose (III) wherein alk is a lower alkyl group containing 1 to 6 carbon atoms which can be straight chain or branched in a non-polar organic solvent selected from the group consisting of dichloroethane and acetonitrile in the presence of a hydrochloric acid acceptor selected from the group consisting of an amine, Lewis base and molecular sieve at a temperature between about 75°-100° C. to produce 2,6-di(alkoxyacetamido)-9-(2,35-tri-O-benzyl-beta-D-arabinofuranosyl) purine (IV) in a first reaction mixture; and
   (b) separating (IV) from the first reaction mixture by removing the non-polar organic solvent; and
   (c) removing 2,6-dialkoxyacet- groups from intermediate (IV) by reaction with sodium methoxide in a lower alkanol selected from the group consisting of ethanol and methanol at a temperature which produces the compound (V).

2. A process for the preparation of 2,6-diamino-9-(2,3,5-tri-O-benzyl-beta-D-arabinofuranosyl) purine (V) which comprises:
   (a) reacting 2,6-di(alkoxyacetamido)purine (II) with 2,3,5-tri-O-benzyl-1-chloro-alpha-D-arabinofuranose (III) wherein alk is a lower alkyl group containing 1 to 6 carbon atoms which can be straigth chain or branched in a non-polar organic solvent selected from the group consisting of dichloroethane and acetonitrile in the presence of a hydrochloric acid acceptor selected from an amine, Lewis base and molecular sieve at a temperature between about 75°-100° C. to produce 2,6-di(alkoxyacetamido)-9-(2,3,5-tri-O-benzyl-beta-D-arabinofuranosyl)purine (IV) in a first reaction mixture; and
   (b) separating (IV) from the first reaction mixture by removing the non-polar organic solvent;
   (c) reacting (IV) with sodium methoxide in a lower alkanol selected from the group consisting of ethanol and methanol at a temperature between about 45° to 55° C. to produce (V) in a second reaction mixture; and
   (d) separating (V) from the seond reaction mixture by removing the lower alkanol.

3. The process of claim 2 wherein the organic solvent is dichloroethane and wherein the lower alkanol is methanol.

4. The process of claim 2 wherein the acid acceptor is diisopropylethylamine provided in the organic solvent.

5. The process of claim 3 wherein the acid acceptor is a molecular sieve provided in the organic solvent.

6. The process of claim 2 wherein the organic solvent is dichloroethane and wherein the acid acceptor is diisopropylethylamine and wherein the reaction is conducted at a temperature between about 80° and 85° C.

7. The process of claim 2 wherein the organic solvent is dichloroethane and wherein the first reaction mixture is refluxed for at least about 18 hours.

8. The process of claim 7 wherein the first reaction mixture after being refluxed is extracted with water which is separated from the first reaction mixture and then (IV) is separated from the organic solvent.

9. The process of claim 8 wherein n-propanol is provided in the first reaction mixture after the water is separated from the reaction mixture to azeotrope the remaining water and dichloroethane in the organic solvent and then the n-propanol is removed from the reaction mixture.

10. The process of claim 2 wherein the lower alkanol is methanol in the second reaction mixture and wherein the second reaction mixture is held at the temperature between about 45° and 55° C. for at least about 3 hours and held at ambient temperature for at least about 18 hours.

11. The process of claim 2 wherein the organic solvent is dichloroethane, wherein the first reaction mixture is refluxed for at least about 18 hours, wherein the lower alkanol in the second reaction mixture is methanol and wherein the second reaction mixture is maintained at the temperature between about 45° and 55° C. for at least about 3 hours.

12. The process of claim 11 wherein the first reaction mixture after being refluxed is extracted with water.

13. The process of claim 12 wherein n-propanol is provided in the first reaction mixture after the water is separated from the first reaction mixture to azeotrope remaining water and dichloroethane in the organic solvent and then the n-propanol is removed from the reaction mixture.

14. The process of claim 2 wherein alk is a methyl group.

15. The compound 2,6-di(alkoxyacetamido)-9-(2,3,5-tri-O-benzyl-beta-D-arabinofuranosyl) purine.

16. The compound of claim 15 wherein alk is a methyl group.

17. The process of claim 1 wherein in addition the 2-amino group of (V) is replaced with a 2-fluoro group by reaction with fluoroboric acid in an organic solvent for the reaction to form 9-(2,3,5 tri-O-benzyl-beta-D-arabinofuranosyl)-2-fluoroadenine (VI) and wherein (VI) is treated in a reaction mixture with hydrogen and palladium chloride in an organic solvent and in a sealed vessel under pressure to produce 9-beta-D-arabinofuranosyl-2-fluoroadenine (VII) which is separated from the reaction mixture.

18. The process of claim 17 wherein the organic solvent is methoxyethanol.

* * * * *

UNITED STATES PATENT AND TRADEMARK OFFICE
CERTIFICATE OF CORRECTION

PATENT NO. : 5,110,919

DATED : May 5, 1992

INVENTOR(S) : Peter Blumbergs, et al

It is certified that error appears in the above-indentified patent and that said Letters Patent is hereby corrected as shown below:

Column 3, lines 5-10, the ring structure should be numbered at the top with a --6--, rather than a "2".

Column 6, line 31, "the", first occurrence, should be --that--.

Column 6, line 44, "D-arabinofuranoxyl)" should be --D-arabinofuranosyl)--.

Column 7, line 60, "mp 155°-7°C.," should be --mp 155°-157°C.,--.

Column 9, line 46, a period --.-- should be inserted after "(1h)" and before "The".

Column 9, line 59, a period --.-- should be inserted after "3 x 500 mL)" and before "The".

Column 9, line 63, "prduct" should be --product--.

Column 12, line 17, "straigth" should be --straight--.

Signed and Sealed this

Seventh Day of September, 1993

Attest:

BRUCE LEHMAN

*Attesting Officer*  Commissioner of Patents and Trademarks